United States Patent [19]
Ishibashi et al.

[11] Patent Number: 4,912,002
[45] Date of Patent: Mar. 27, 1990

[54] ELECTROPHOTOSENSITIVE LAYERED ARTICLE PROVIDED STYRYL COMPOUNDS AND BISAZO PIGMENT

[75] Inventors: Setsuo Ishibashi; Katsunori Fujio, both of Furukawa; Yorihiko Sasaki, Miyagi, all of Japan

[73] Assignee: Alps Electric Co., Ltd., Tokyo, Japan

[21] Appl. No.: 228,881

[22] Filed: Aug. 4, 1988

[30] Foreign Application Priority Data

Nov. 30, 1987 [JP] Japan .................................. 62-302787

[51] Int. Cl.$^4$ ............................................ G03G 5/06
[52] U.S. Cl. ........................................ 430/76; 430/58
[58] Field of Search ..................................... 430/58, 76

[56] References Cited

U.S. PATENT DOCUMENTS

| | | | |
|---|---|---|---|
| 4,251,613 | 2/1981 | Sasaki et al. | 430/72 |
| 4,251,614 | 2/1981 | Sasaki et al. | 430/79 |
| 4,293,628 | 10/1981 | Hashimoto et al. | 430/58 |
| 4,481,271 | 11/1984 | Hashimoto | 430/58 X |
| 4,540,651 | 9/1985 | Fujimuki et al. | 430/58 X |

*Primary Examiner*—J. David Welsh
*Attorney, Agent, or Firm*—Guy W. Shoup; Paul J. Winters; David W. Heid

[57] ABSTRACT

According to the present invention, by using in combination a styryl compound expressed by general formula [I] or [II] and a bisazo pigment expressed by general formula [III] below, a highly sensitive and durable photoconductive coat which exhibits a low residual electric potential and is free from deterioration caused by fatigue through repeated use and an electrophotosensitive article provided with such a coat are obtained.

Therefore, the present invention finds its applications in electronic photocopying devices, laserbeam printers, LED printers, CRT printers and other devices of electronic photography.

2 Claims, 5 Drawing Sheets

ELECTROPHOTOSENSITIVE LAYERED ARTICLE PROVIDED STYRYL COMPOUNDS AND BISAZO PIGMENT

BACKGROUND OF THE INVENTION

1. Field of the Invention

The present invention relates to a photoconductive coat containing specific organic photoconductive compounds and an electrophotosensitive article provided with such a coat.

2. Description of the Prior Art

Electrophotosensitive articles having a photosensitive layer containing inorganic photoconductive compounds such as selenium, zinc oxide, cadmium sulfide and the like as main ingredients have been widely known. However, such known articles are not necessarily satisfactory in terms of thermal stability, durability and other properties and accompanied by manufacturing and handling problems because of toxicity of these compounds.

On the other hand, electrophotosensitive articles having a photosensitive layer containing organic photoconductive compounds as major ingredients have been attracting attention because such articles offer a number of advantages including relative ease of manufacture, relatively low cost, non existence of handling problems and thermal stability that photosensitive elements containing selenium. One of the most popular organic photoconductive compounds for this purpose is poly-N-vinylcarbazole, which is used with Lewis acid of 2,4,7-trinitro-9-freorenon or other substances to form a charge transfer complex material, which is in turn used as a major ingredient of a photosensitive layer of an electrophotosensitive article. Electrophotosensitive articles of this type are already commercially available.

Electrophotosensitive articles having a functionally divided photosensitive layer of either two-layered type or dispersed type, in which the electric charge generation function and the electric charge transfer function are respectively carried by different materials, are also known. For instance, an electrophotosensitive article having a photosensitive layer comprising an electric charge generation layer consisting of a thin film of amorphous selenium and an electric charge transfer layer containing poly-N-vinylcarbazole as a major ingredient is already marketed.

Efforts have been paid to realize an electrophotosensitive article having a functionally divided photosensitive layer as described above by using organic photoconductive compounds for both electric charge generation materials and electric charge transfer materials. Some of the organic compounds that can be used as electric charge generation materials include azo pigments, phthalocyanine pigments, anthraquinone pigments, perylene pigment, cyanine pigment, thiapyrylium pigment and squarium pigment, while some of the organic compounds that can be used for electric charge transfer materials include amine derivatives, oxazol derivatives, triphenylmethane derivatives and hydrazone derivatives.

These electric charge generation and electric charge transfer materials are used with a variety of binding materials to form a film layer as they are not capable of forming a film by themselves. Two types of electrophotosensitive articles are known, a two-layered type having an electric charge generation layer and an electric charge transfer layer formed on an electroconductive support and a dispersed type having a layer containing a certain amount of an electric charge generation material and an electric charge transfer material in a dispersed condition.

However, there are currently few electrophotosensitive articles containing organic photoconductive compounds as electric charge generation materials which are feasible for practical use as they are generally less photoconductive and less durable as compared with those containing inorganic photoconductive compounds.

The object of the present invention is to solve the above mentioned problem by providing a photoconductive coat which is highly sensitive and accompanied by a low residual electric potential and an electrophotosensitive article provided with such a coat which, when used for electric photography in which electric charging, light exposure, development and copy printing processes are repeatedly conducted, exhibits an excellent durability as it is relatively free from deterioration caused by fatigue through repeated use and maintains its original photoconductive characteristics for a long term.

SUMMARY OF THE INVENTION

A photoconductive coat according to the present invention is characterized in that it contains at least a styryl compound which is expressed by general formula [I] or [II] below and at least a bisazo pigment which is expressed by general formula [III] below.

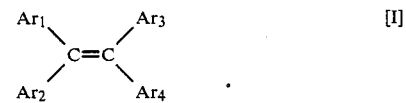

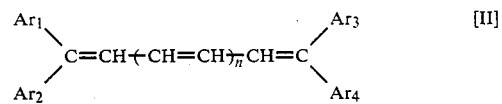

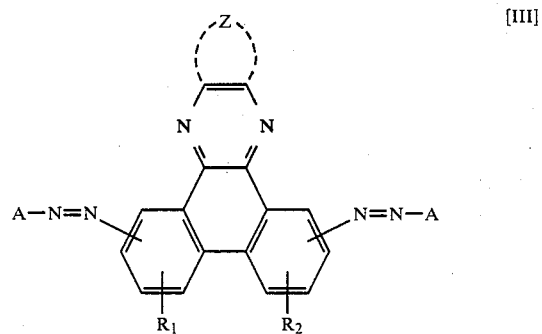

wherein each of $Ar_1$, $Ar_2$, $Ar_3$ and $Ar_4$ represents an aryl group that may possess a substituent, n is 0 or 1, each of $R_1$ and $R_2$ represents a hydrogen atom, a lower alkyl group, an aryl group, an alkoxycarbonyl group, an acyl group, a halogen atom or a monovalent organic residue, Z represents an atomic group necessary to form a substituted or non-substituted hydrocarbon or heterocyclic aromatic ring through condensation with a pyrazine ring, A represents

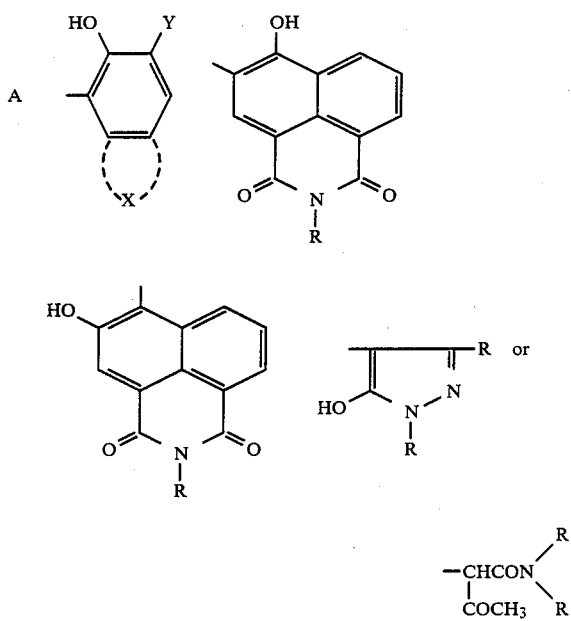

X represents an atomic group necessary to form a substituted or non-substituted hydrocarbon or heterocyclic aromatic ring through condensation with a benzene ring, Y represents

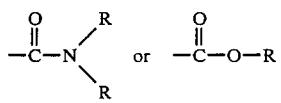

R represents a hydrogen atom, a lower alkyl group, an aryl group, an alkoxycarbonyl group, an allyloxycarbonyl group, an acyl group, a halogen atom or a monovalent organic residue that may be identical or different.

An electrophotosensitive article according to the present invention is provided on its electroconductive support member with a photosensitive layer comprising a photoconductive coat containing at least a styryl compound expressed by said general formula [I] or [II] as an electric charge transfer material and at least a bisazo pigment expressed by said general formula [III] to solve the above described problems.

DETAILED DESCRIPTION OF THE INVENTION

The inventors of the prevent invention have, after an intensive study, come to find that the above mentioned object is achieved by providing a photosensitive coat containing at least a styryl compound expressed by said general formula [I] or [II] as an electric charge transfer material and at least a bisazo pigment expressed by said general formula [III] and an electrophotosensitive article provided with such a coat.

Namely, by using in combination a styryl compound expressed by said general formula [I] or [II] and a bisazo pigment expressed by said general formula [III] according to the present invention, a highly sensitive and durable photoconductive coat which exhibits a low residual electric potential and is free from deterioration caused by fatigue through repeated use and an electrophotosensitive article provided with such a coat are obtained.

Some examples of styryl compounds which are expressed by said general formula [I] include

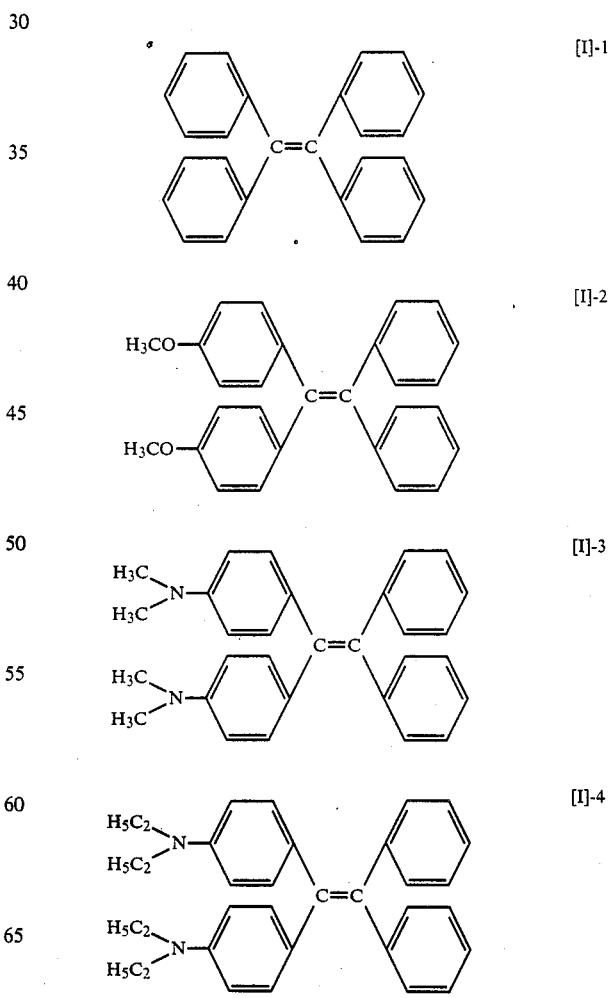

-continued
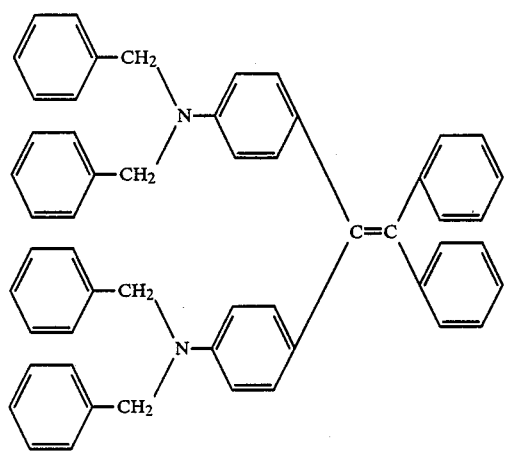  [I]-5
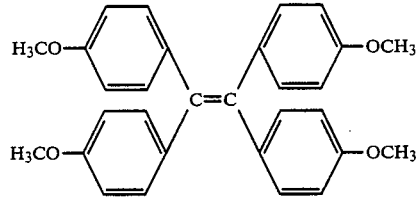  [I]-6
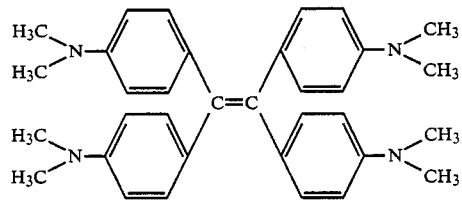  [I]-7
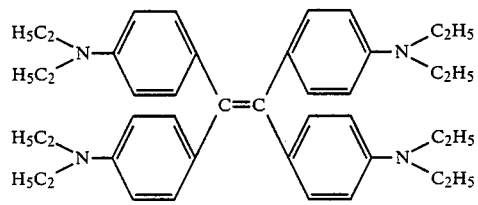  [I]-8
Some examples of styryl compounds which are expressed by said general formula [II] include
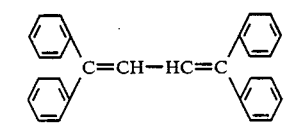  [II]-1
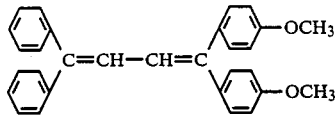  [II]-2
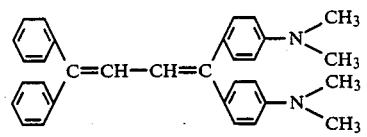  [II]-3
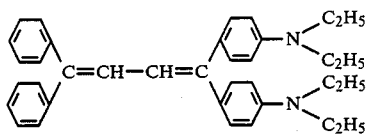  [II]-4
[II]-5
[II]-6
[II]-7
[II]-8
[II]-9
[II]-10
[II]-11

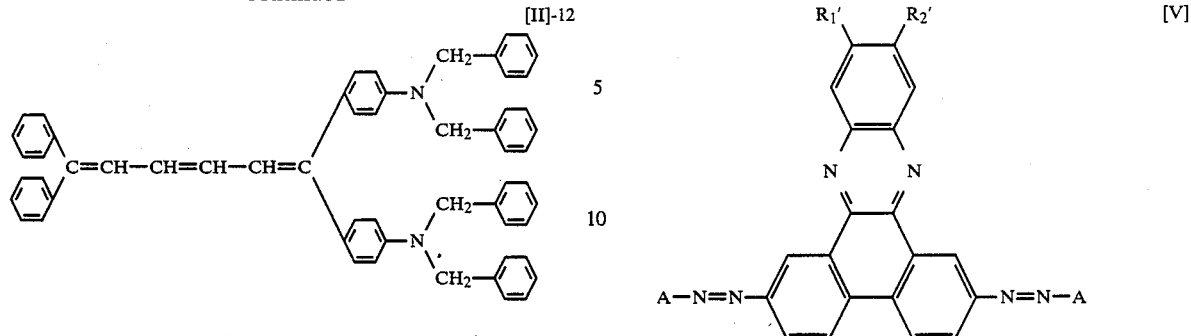
[II]-12

Some examples of bisazo pigments which are expressed by said general formula [III] include

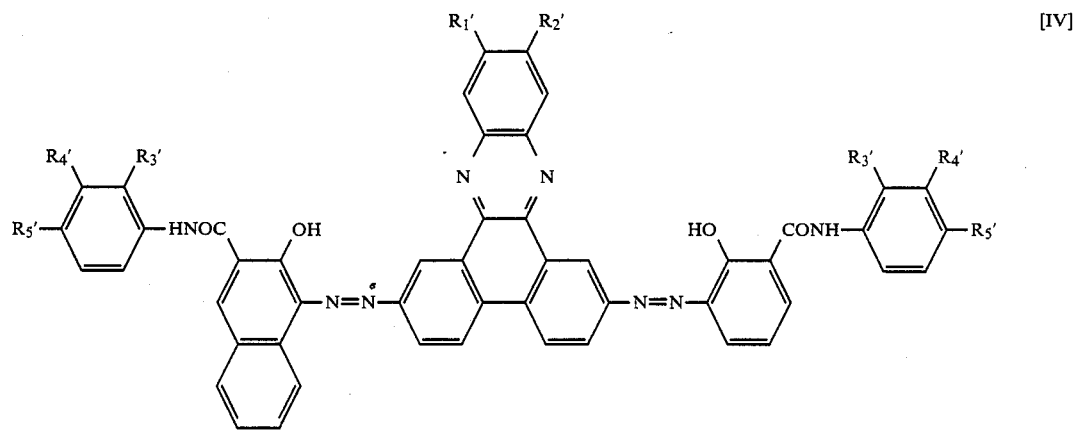
[IV]

[V]

Examples of atoms and groups which are represented by $R'_1$, $R'_2$, $R'_3$, $R'_4$ and $R'_5$ in the above expression are shown in the accompanying Table 1.

Examples of atoms and groups which are represented by $R'_1$, $R'_2$ and A in the above expression are shown in the accompanying Table 2.

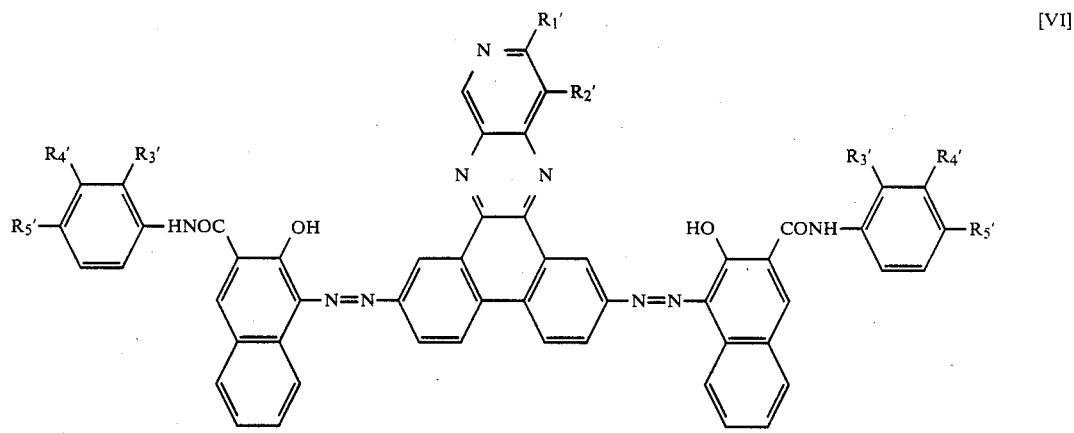
[VI]

Examples of atoms and groups which are represented by $R'_1$, $R'_2$, $R'_3$, $R'_4$ and $R'_5$ in the above expression are shown in the accompanying Table 3.

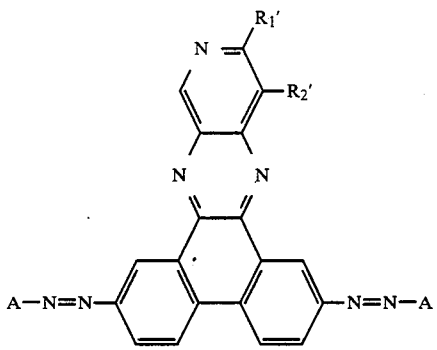

Examples of atoms and groups which are represented by $R'_1$, $R'_2$ and A in the above expression are shown in the accompanying Table 4.

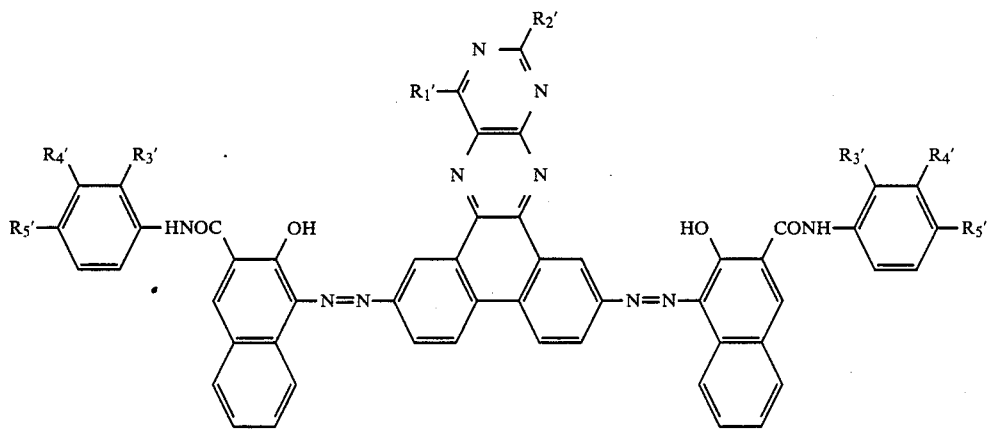

Examples of atoms and groups which are represented by $R'_1$, $R'_2$, $R'_3$, $R'_4$ and $R'_5$ in the above expression are shown in the accompanying Table 5.

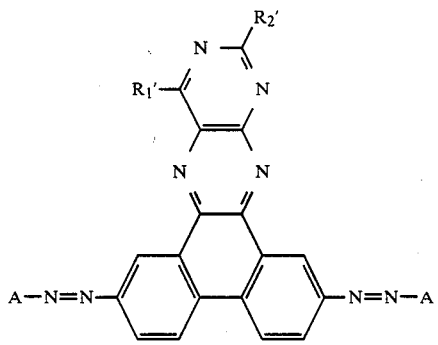

Examples of atoms and groups which are represented by $R'_1$ and A in the above expression are shown in the accompanying Table 6.

It should be noted that styryl compounds and bisazo pigments that can be used for a photoconductive coat according to the present invention are not limited to the examples shown herein.

Figure 7:
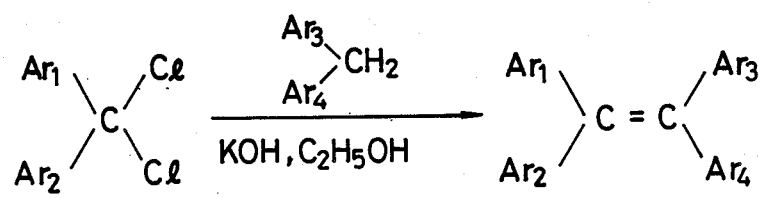
FIGS. 7 and 8 illustrate the processes for synthetically producing styryl compounds which are expressed by general formulas [I] and [II] respectively.
Figure 8:
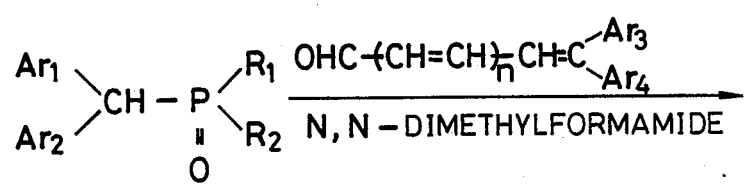
Figure 8:
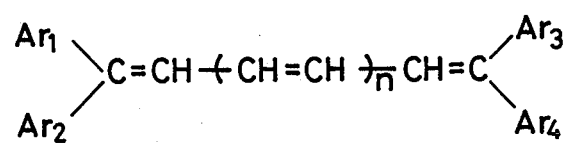
Figure 9:
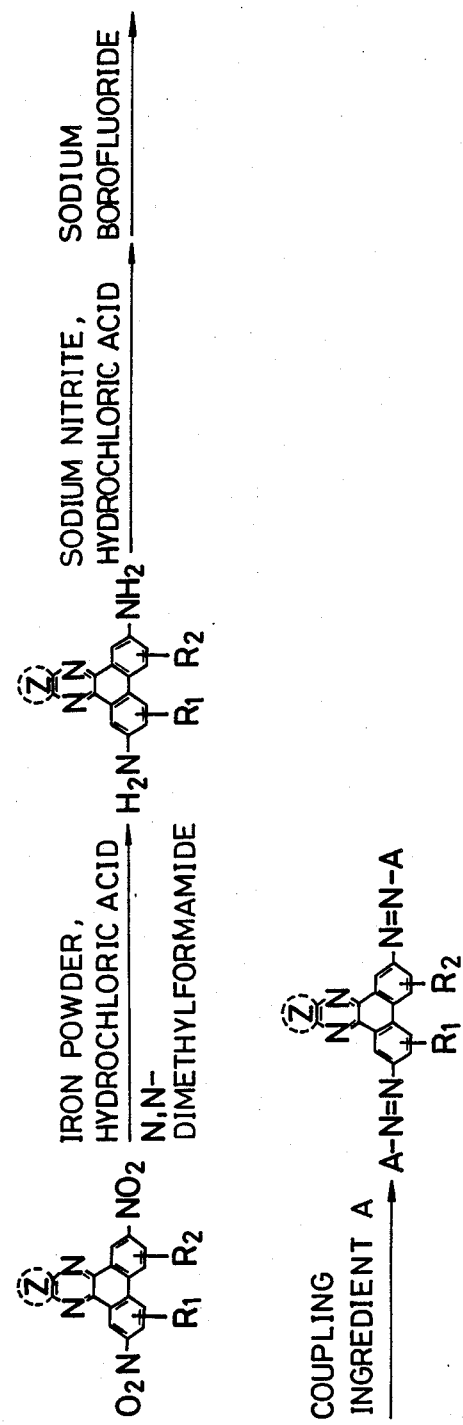
FIG. 9 illustrates the process for synthetically producing bisazo pigments which are expressed by general formula [III].

It is known that styryl compounds which are expressed by said general formula [I] can be synthetically produced through the process as shown in FIG. 7 and those which are expressed by said general formula [II] can be produced through the process as shown in FIG. 8. In order to obtain a bisazo pigment as expressed by said general formula [III], an appropriate dinitro compound is reduced with iron or tin to form a diamino compound, which is then processed to form a bisazo compound. The corresponding bisazo pigment can be obtained either by directly coupling the compound or by isolating with sodium borofluoride and then conducting coupling in an alkaline condition in a N,N-dimethylformamide solution. The symbols in the formulas in FIGS. 7, 8 and 9 respectively denote the same atoms and groups as those in said general formulas [I], [II] and [III].

An electrophotosensitive article according to the present invention comprising a styryl compound expressed by said general formula [I] or [II] as an electric charge transfer material and a bisazo pigment expressed by said general formula [III] as an electric charge generation material can, for example, have any of the following configurations.

Figure 1:
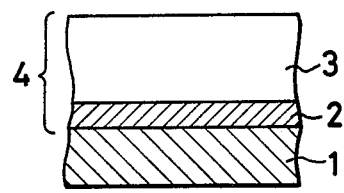
FIGS. 1 through 6 are enlarged sectional views illustrating configurations of different embodiments of the electrophotosensitive article according to the present invention.
Figure 2:
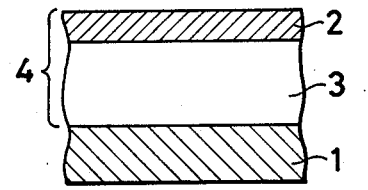

In the configurations shown in FIGS. 1 and 2, two strata photosensitive layer 4 consisting of electric charge generation layer 2 containing an electric charge generation material as a major ingredient and electric charge transfer layer 3 containing an electric charge transfer material as a major ingredient is formed on electroconductive support member 1. While electric charge transfer layer 3 is placed on electric charge generation layer 2 in FIG. 1, the latter is placed on the former in FIG. 2.

Figure 3:
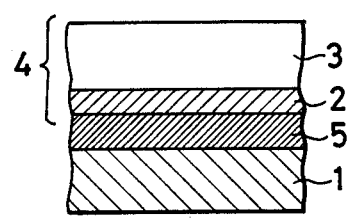
Figure 4:
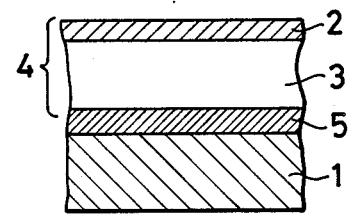

FIGS. 3 and 4 shows two different configurations comprising intermediate layer 5 between electroconductive support member 1 and photosensitive layer 4 which is a two-strata layer as in the case of FIGS. 1 and 2.

Figure 5:
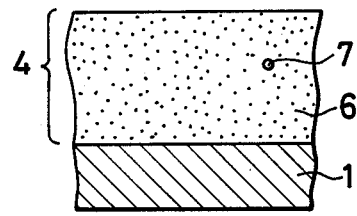
Figure 6:
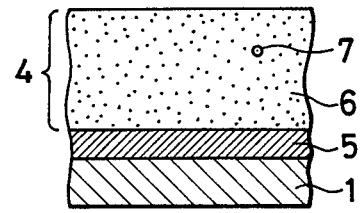

FIGS. 5 and 6 show two different configurations having photosensitive layer 4, which is practically layer 6 consisting of an electric charge transfer material as a major ingredient in which granules of an electric generation material are dispersed, placed directly or via an intermediary of intermediate layer 4 on electroconductive support member 1.

Electroconductive support member 1 is typically made of a metal plate, a plate of an electroconductive compound such as electroconductive polymer, indium oxide or a sheet of paper or plastic which is rendered electroconductive by applying, through vapor disposition of or by laminating a foil of aluminum, palladium, gold or the like.

Electric charge generation layer 2 is formed either by applying a dispersion solution obtained by granulating electric charge generating material 7 which is expressed by said general formula [III] in a dispersion medium through use of a ball mill, a homomixer, a sand mill or a coloid mill and by dispersing as a mixture of an binding agent if required onto support member 1. Alternatively, it is formed by applying solution which is obtained by dissolving electric charge generation material 7 into a binding agent in a solvent onto support member 1 by using a technique of dipping, spraying or spinning.

Bonding agents that can be used for this purpose include but not limited to phenol resin, polyester resin, acetic acid vinyl resin, polycarbonate resin, polypeptide resin, cellulose resin, polyvinyl pyrrolidone, polyethylene oxide, polyvinyl chloride resin, various types of starch, polyvinyl alcohol, acrylic copolymer resins, methacrylic copolymer resins, silicone resin, polyacrylic nitrile copolymer resins, polyacrylic amide and polyvinyl butyral. These agents can be used individually or in combination of two or more than two thereof.

Electric charge generation layer 2 may also be formed by producing a thin film of bisazo pigment as expressed by said general formula [III] by using a vacuum vapor deposition technique.

Electric charge transfer layer 3 is formed by applying solution of an electric charge transfer material as expressed by said general formula [I] or [II] which is dispersedly dissolved into a binding agent onto support member 1.

Binding agents that can be used for this purpose include but are not limited to phenol resin, polyester resin, acetic acid vinyl resin, polycarbonate resin, polypeptide resin, cellulose resin, polyvinyl pyrrolidone, polyethylene oxide, polyvinyl chloride resin, various types of starch, plyvinyl alcohol, acrylic copolymer resins, methacrylic copolymer resins, silicone resin, polyacrylic nitrile copolymer resin, polyacrylic amide and polyvinyl butyral. These binding agents may be used individually or in combination of two or more than two thereof.

Intermediate layer 5 placed between electroconductive support member 1 and photosensitive layer 4 is designed to function as a barrier as well as an adhesive and is typically made of casein, polyvinyl alcohol, nitrocellulose, ethylene acrylic acid copolymer, polyamides (such as nylon 6, nylon 66, nylon 610, copolymeric nylon and alkoxymethylated nylon), polyurethane, gelatin or aluminium oxide.

Photosensitive layer 4, which is practically layer 6 containing an electric charge transfer material as major ingredient in which granules of electric charge generation material 7 are dispersed as described above, can be formed by either dispersing or dissolving the electric charge transfer material, thereafter dispersing electric charge generation material 7 into any of the above listed binding agents and then applying the obtained solution onto support member 1.

Now examples embodying the present invention will be given in the following to describe the invention in greater detail. However, it should be noted that the present invention is not limited to these embodiments.

DESCRIPTION OF THE PREFERRED EMBODIMENTS

Example 1

1 weight portion of bisazo pigment No. [IV]-1 as listed in Table 1, 1 weight portion of silicone resin (product of SIN-ETSU CHEMICAL CO., LTD., EN-1001N) and 50 weight portions of tetrahydrofuran were put into a planetary ball mill (product of FRITSCH LABORGERÄTEBAU, P-6) and subjected to a dispersion treatment for six hours to obtain a solution of an electric charge generation material to be used for application.

The solution was applied with an electric applicator (product of RIKEN SEIMITSU CO., LTD.) onto an aluminum plate that had been cleaned by using an UV technique for degreasing (product of TOYO ALUMINIUM LIMITED). A doctor blade having a gap of 100 $\mu$m was used with the applicator for application of the solution. Thereafter the coat of the applied solution was dried at 40° C. for 30 minutes and then at 80° C. for an hour to obtain an electric charge generation layer having a thickness of 0.2 to 0.4 $\mu$m.

Apart from this, 1 weight portion of styryl compound No. [II]-3 and 1 weight portion of polycarbonate resin (product of MITSUBISHI CHEMICAL INDUSTRIES LIMITED, NOVAREX 7030A) were dissolved in 6 weight portions of a mixture of dichloromethane and chlorobenzene to obtain a solution of an electric charge transfer material to be used for application. The solution was then applied onto the electric charge generation layer by using a 100 $\mu$m gap doctor blade. Thereafter the plate was dried at 40° C. for 30 minutes and then at 80° C. for 6 hours to obtain an electric charge transfer layer having a thickness of 18 $\mu$m.

The prepared photosensitive specimen was then subjected to an evaluation test using a charged static electricity tester (product of KAWAGUCHI ELECTRIC WORKS CO., LTD., EPA-8100), in which electricity of $-28$ $\mu$A was supplied to the corona charging unit statically for discharging.

Firstly, the specimen was tested for its spectral sensitivity. For measurement of spectral sensitivity, a light source was masked with an optical interference filter (product of TOSHIBA CORP., KL) to produce desired monochromatic lights of various wavelengths in such a manner that a light having an energy of 2.7 $\mu$W/cm$^2$ is irradiated for each wavelength. The photosensitivity of the specimen was determined by measuring its sensitivity $E_{1/2}$ ($\mu$J/cm$^2$) or the amount of light energy required to halve the charged potential of $-700$ V. The test result is shown in Table 8.

Thereafter, ① initial charged potential $V_0$ (V), ② sensivity $E_{1/2}$ (lux.s) to be determined by measuring the period of time required to halve the charged potential of approximately $-700$ V after irradiating white light of 5 lux and ③ residual potential $V_r$ (V) which is the surface potential 10 seconds after starting light irradiation were determined. The retention ratio of the specimen was also determined by measuring the charged potential before and after irradiation of white light of 1250 lux for 30 minutes to know its anti-light degradation characteristics. Table 7 shows the result of these measurements.

Figure 12:
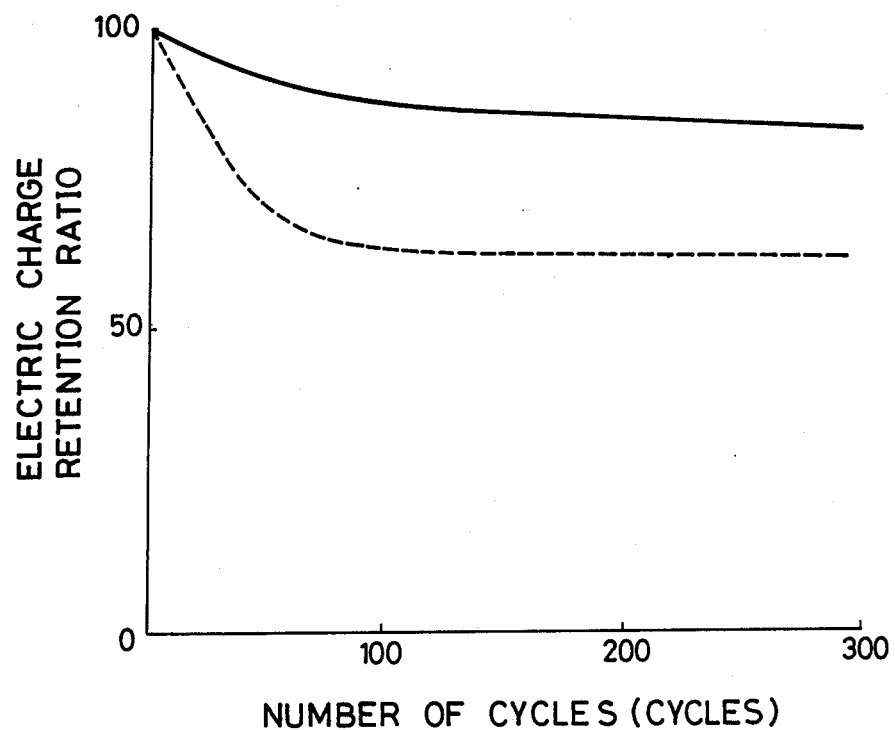

Finally, its repetition characteristics were determined by observing the charged potential after repetition of numbers of times and calculating ratios (%) of the measured potentials to the initial potential. The repetition characteristics are shown in FIG. 12.

Comparison Example

For the purpose of comparison, a photosensitive specimen was prepared in the same manner as described for Example 1 above by using identical materials except that chlorodyeanblue (CDB) was used in place of bisazo pigment No. [IV]-1 and the obtained specimen was subjected to a number of tests as described for Example 1 to determine its characteristics.

Figure 10:
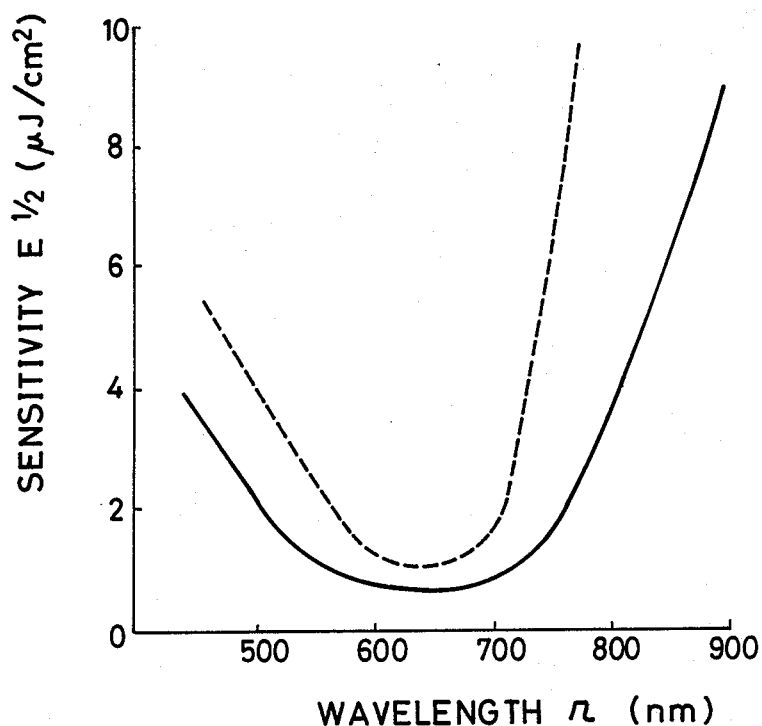
FIG. 10 is a graphic illustration of the spectral sensitivity of the specimen of Example 1.
Figure 11:
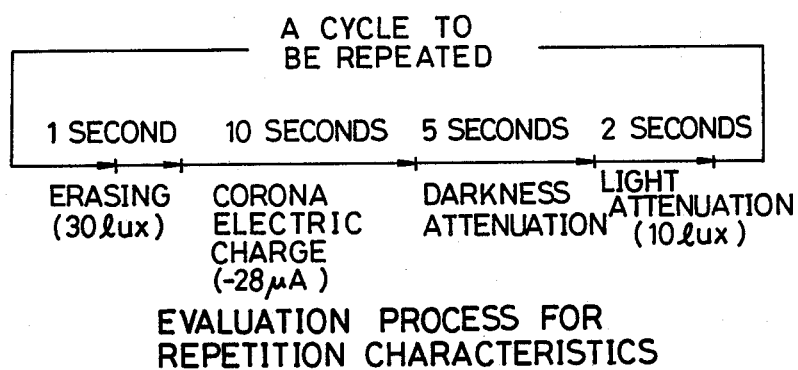
FIG. 11 illustrates the process for determining the repetition characteristics of the specimen of Example 1 and FIG. 12 is a graphic illustration of the repetition characteristics of the specimen of Example 1.

The test results are shown in Table 7 below as well as in accompanying FIGS. 10 and 12, in which solid lines are used for Example 1 whereas broken lines are for Comparison Example.

TABLE 7

|  | Example 1 | Comparison Example |
|---|---|---|
| initial charged potential $V_0$ (V) | −780 | −720 |
| photosensitivity $E_{\frac{1}{2}}$(lux · s) | 1.2 | 1.8 |
| residual potential Vr(V) | 0 | −25 |
| anti-light degradation $V_0$ (%) | 95 | 90 |

From these results, it became apparent that by combining a styryl compound which is expressed by either said general formula [I] or [II] and a bisazo pigment which is expressed by said general formula [III] an electrophotosensitive article which is electrically highly charged and highly photosensitive, shows a low residual potential level and possesses excellent repetition as well as anti-light degradation characteristics can be obtained.

Examples 2 through 15

Electrophotosensitive specimens were prepared in the same manner as described for Example 1 by using bisazo pigments respectively listed in Table 8 in place of bisazo pigment No. [IV]-1 as electric charge generation materials and also styryl compounds respectively listed in Table 8 in place of styryl compound No. [II]-3. The initial charged potential, the sensitivity and the residual potential of each of these electrophotosensitive specimens were measured to determine their characteristics. The results are shown in Table 8.

Whereas all the electrophotosensitive specimens of Examples 2 through 15 possessed excellent characteristics, those of Examples 5, 7, 13 and 15 exhibited an excellent electric charge, a good sensitivity and a low residual potential to prove that they are particularly suitable for use as electrophotosensitive articles.

TABLE 8

| Example No. | Styryl Compound No. *1 | Bisazo Pigment No. *2 | Initial Potential $V_0$ (−V) | Sensitivity $E_{\frac{1}{2}}$(lux · s) | Residual Potensial $V_R$(−V) |
|---|---|---|---|---|---|
| 2 | [I]-3 | [IV]-1 | 770 | O | 0 |
| 3 | [I]-4 | [IV]-10 | 760 | O | 0 |
| 4 | [I]-5 | [V]-8 | 890 | O | 0 |
| 5 | [I]-7 | [VI]-22 | 810 | O | 0 |
| 6 | [I]-6 | [VII]-9 | 600 | Δ | 0 |
| 7 | [I]-8 | [VIII]-2 | 920 | O | 0 |
| 8 | [I]-10 | [IX]-8 | 810 | O | 0 |
| 9 | [II]-3 | [IV]-1 | 810 | O | 0 |
| 10 | [II]-4 | [IV]-10 | 790 | O | 0 |
| 11 | [II]-5 | [V]-8 | 800 | O | 0 |
| 12 | [II]-7 | [VI]-22 | 760 | O | 0 |
| 13 | [II]-6 | [VII]-12 | 900 | O | 0 |
| 14 | [II]-8 | [VIII]-38 | 320 | X | 10 |
| 15 | [II]-12 | [IX]-8 | 900 | O | 0 |

*1 Each of the numbers in this column denotes the reference number of the chemical formula of a styryl compound shown in the text.
*2 Each of the numbers in this column denotes a combination of the reference number of the chemical formula of a bisazo compound and the number of a coupler shown in Tables 1 and 6.
The symbols in the column of sensitivity denote as follows: O: $E_{\frac{1}{2}} < 2$, Δ: $2 \leq E_{\frac{1}{2}} < 10$ X: $10 \leq E_{\frac{1}{2}}$ The specimens of Examples 2 through 15 were as excellent as the specimen of Example 1 in terms of repetition characteristics and anti-light degradation characteristics.

TABLE 1

| Coupler No. | $R'_1$ | $R'_2$ | $R'_3$ | $R'_4$ | $R'_5$ | Coupler No. | $R'_1$ | $R'_2$ | $R'_3$ | $R'_4$ | $R'_5$ |
|---|---|---|---|---|---|---|---|---|---|---|---|
| [IV]-1 | H | H | H | H | H | [IV]-21 | CH$_3$ | H | H | H | H |
| 2 | H | H | Cl | H | H | 22 | CH$_3$ | CH$_3$ | H | H | H |
| 3 | H | H | H | Cl | H | 23 | CH$_3$ | H | Cl | H | H |
| 4 | H | H | H | H | Cl | 24 | CH$_3$ | H | H | H | NO$_2$ |
| 5 | H | H | F | H | H | 25 | CH$_3$ | H | CH$_3$ | H | H |
| 6 | H | H | H | F | H | 26 | CH$_3$ | CH$_3$ | Cl | H | H |
| 7 | H | H | H | H | F | 27 | CH$_3$ | CH$_3$ | H | H | NO$_2$ |
| 8 | H | H | NO$_2$ | H | H | 28 | CH$_3$ | CH$_3$ | CH$_3$ | H | H |
| 9 | H | H | H | NO$_2$ | H | 29 | CH$_3$ | H | H | CH$_3$ | Cl |
| 10 | H | H | H | H | NO$_2$ | 30 | CH$_3$ | CH$_3$ | CH$_3$ | H | Cl |
| 11 | H | H | CH$_3$ | H | H | 31 | CN | H | H | H | H |
| 12 | H | H | H | CH$_3$ | H | 32 | CN | CN | H | H | H |
| 13 | H | H | H | H | CH$_3$ | 33 | CN | H | CH$_3$ | H | H |
| 14 | H | H | C$_2$H$_5$ | H | H | 34 | CN | H | H | H | Cl |
| 15 | H | H | H | C$_2$H$_5$ | H | 35 | CN | H | H | H | NO$_2$ |
| 16 | H | H | H | H | C$_2$H$_5$ | 36 | CN | CN | H | H | Cl |
| 17 | H | H | OCH$_3$ | H | H | 37 | OH | H | H | H | H |
| 18 | H | H | H | OCH$_3$ | H | 38 | OH | OH | H | H | H |
| 19 | H | H | H | H | OCH$_3$ | 39 | OH | H | CH$_3$ | H | H |
| 20 | H | H | CH$_3$ | H | Cl | 40 | OH | OH | H | H | Cl |

TABLE 2

| Coupler No. | R₁' | R₂' | A |
|---|---|---|---|
| (V)-1 | H | H | 3-hydroxy-4-methyl-5-(2-aminophenyl-NH-)-N-phenylbenzamide structure |
| 2 | H | H | 3-hydroxy-4-methyl-5-(2-aminophenyl-NH-)-N-(2-methylphenyl)benzamide structure |
| 3 | CH₃ | H | 3-hydroxy-4-methyl-N-phenyl-2-anthracenecarboxamide structure |
| 4 | H | H | 3-hydroxy-4-methyl-N-(1-naphthyl)-2-anthracenecarboxamide structure |

TABLE 2-continued
| Coupler No. | $R_1'$ | $R_2'$ | A |
|---|---|---|---|
| 5 | H | H | 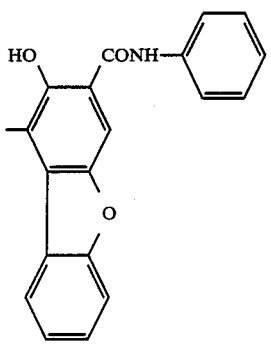 |
| 6 | H | H | 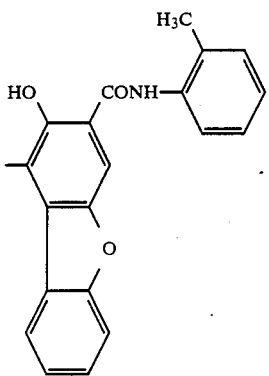 |
| 7 | H | H | 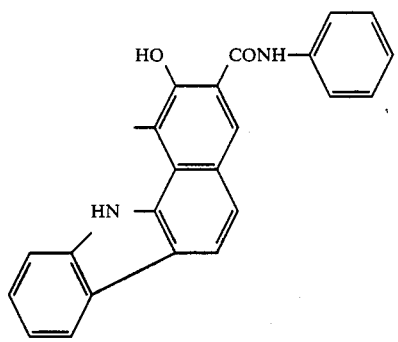 |
| 8 | H | H | 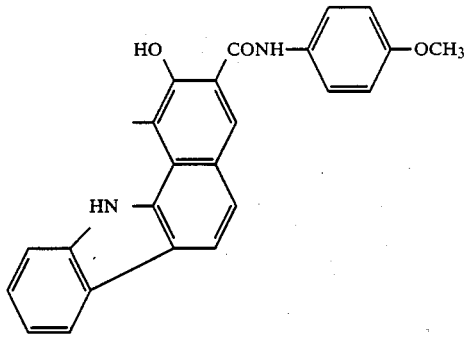 |

TABLE 2-continued

| Coupler No. | $R_1'$ | $R_2'$ | A |
|---|---|---|---|
| 9 | H | H | (structure: 3-hydroxy-4-methyl-5-(phenylamino)-6-phenyl-naphthalene-2-carboxamide with N-(2-methyl-4-methoxyphenyl)) |
| 10 | H | H | (structure: 6-hydroxy-7-methyl-1H-benz[de]isoquinoline-1,3(2H)-dione, N–H) |
| 11 | H | H | (structure: 6-hydroxy-7-methyl-1H-benz[de]isoquinoline-1,3(2H)-dione, N–CH$_3$) |
| 12 | H | H | (structure: 6-hydroxy-7-methyl-1H-benz[de]isoquinoline-1,3(2H)-dione, N–C$_2$H$_5$) |
| 13 | H | H | (structure: 5-hydroxy-6-methyl-1H-benz[de]isoquinoline-1,3(2H)-dione, N–H) |
| 14 | H | H | (structure: 5-hydroxy-6-methyl-1H-benz[de]isoquinoline-1,3(2H)-dione, N–C$_2$H$_5$) |

TABLE 3

| Coupler No. | $R'_1$ | $R'_2$ | $R'_3$ | $R'_4$ | $R'_5$ | Coupler No. | $R'_1$ | $R'_2$ | $R'_3$ | $R'_4$ | $R'_5$ |
|---|---|---|---|---|---|---|---|---|---|---|---|
| [VI]-1 | H | H | H | H | H | [VI]-21 | $CH_3$ | H | H | H | H |
| 2 | H | H | Cl | H | H | 22 | $CH_3$ | $CH_3$ | H | H | H |
| 3 | H | H | H | Cl | H | 23 | $CH_3$ | H | Cl | H | H |
| 4 | H | H | H | H | Cl | 24 | $CH_3$ | H | H | H | $NO_2$ |
| 5 | H | H | F | H | H | 25 | $CH_3$ | H | $CH_3$ | H | H |
| 6 | H | H | H | F | H | 26 | $CH_3$ | $CH_3$ | Cl | H | H |
| 7 | H | H | H | H | F | 27 | $CH_3$ | $CH_3$ | H | H | $NO_2$ |
| 8 | H | H | $NO_2$ | H | H | 28 | $CH_3$ | $CH_3$ | $CH_3$ | H | H |
| 9 | H | H | H | $NO_2$ | H | 29 | $CH_3$ | H | $CH_3$ | H | Cl |
| 10 | H | H | H | H | $NO_2$ | 30 | $CH_3$ | $CH_3$ | $CH_3$ | H | Cl |
| 11 | H | H | $CH_3$ | H | H | 31 | CN | H | H | H | H |
| 12 | H | H | H | $CH_3$ | H | 32 | CN | CN | H | H | H |
| 13 | H | H | H | H | $CH_3$ | 33 | CN | H | $CH_3$ | H | H |
| 14 | H | H | $C_2H_5$ | H | H | 34 | CN | H | H | H | Cl |
| 15 | H | H | H | $C_2H_5$ | H | 35 | CN | H | H | H | $NO_2$ |
| 16 | H | H | H | H | $C_2H_5$ | 36 | CN | CN | H | H | Cl |
| 17 | H | H | $OCH_3$ | H | H | 37 | OH | H | H | H | H |
| 18 | H | H | H | $OCH_3$ | H | 38 | OH | OH | H | H | H |
| 19 | H | H | H | H | $OCH_3$ | 39 | OH | H | $CH_3$ | H | H |
| 20 | H | H | $CH_3$ | H | Cl | 40 | OH | OH | H | H | Cl |

TABLE 4

| Coupler No. | $R_1'$ | $R_2'$ | A |
|---|---|---|---|
| (VII)-1 | H | H | 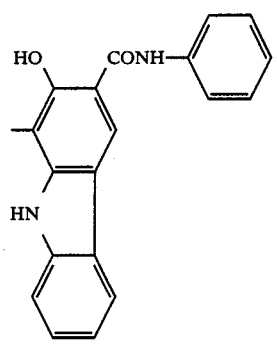 |
| 2 | H | H | 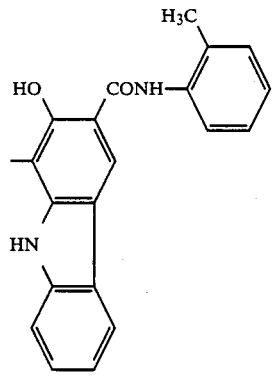 |
| 3 | $CH_3$ | H | 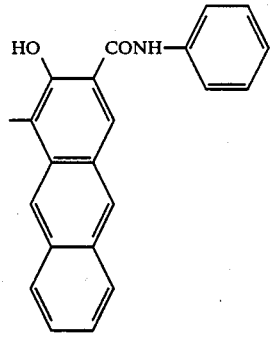 |

TABLE 4-continued

| Coupler | | | |
|---|---|---|---|
| No. | R₁' | R₂' | A |
| 4 | H | H | (3-hydroxy-naphthalene-2-carboxylic acid 1-naphthylamide structure) |
| 5 | H | H | (hydroxy-dibenzofuran carboxanilide structure) |
| 6 | H | H | (hydroxy-dibenzofuran 2-methylphenyl carboxamide structure) |
| 7 | H | H | (hydroxy-carbazole-naphthalene carboxanilide structure) |

TABLE 4-continued

| Coupler No. | R₁' | R₂' | A |
|---|---|---|---|
| 8 | H | H | (3-hydroxy-4-methyl-5-(o-tolylamino)-2-naphthyl)-N-(4-methoxyphenyl)carboxamide structure |
| 9 | H | H | (3-hydroxy-4-methyl-5-(o-tolylamino)-2-naphthyl)-N-(2-methyl-4-methoxyphenyl)carboxamide structure |
| 10 | H | H | 6-hydroxy-5-methyl-1H-benz[de]isoquinoline-1,3(2H)-dione |
| 11 | H | H | 6-hydroxy-5-methyl-2-methyl-1H-benz[de]isoquinoline-1,3(2H)-dione |
| 12 | H | H | 6-hydroxy-5-methyl-2-ethyl-1H-benz[de]isoquinoline-1,3(2H)-dione |

TABLE 4-continued

| Coupler No. | R₁' | R₂' | A |
|---|---|---|---|
| 13 | H | H | 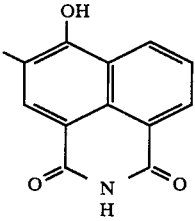 |
| 14 | H | H | 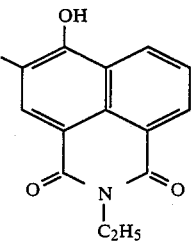 |

TABLE 5

| Coupler No. | $R'_1$ | $R'_2$ | $R'_3$ | $R'_4$ | Coupler No. | $R'_1$ | $R'_2$ | $R'_3$ | $R'_4$ |
|---|---|---|---|---|---|---|---|---|---|
| [VIII]-1 | H | H | H | H | [VIII]-16 | $CH_3$ | $CH_3$ | H | $NO_2$ |
| 2 | H | Cl | H | H | 17 | $C_2H_5$ | Cl | H | H |
| 3 | H | H | Cl | H | 18 | $C_2H_5$ | H | H | $NO_2$ |
| 4 | H | H | H | Cl | 19 | $C_2H_5$ | $CH_3$ | H | H |
| 5 | H | H | H | $NO_2$ | 20 | $C_2H_5$ | $CH_3$ | H | Cl |
| 6 | H | $CH_3$ | H | H | 21 | $C_2H_5$ | $CH_3$ | H | $NO_2$ |
| 7 | H | $CH_3$ | H | Cl | 22 | $C_2H_5$ | H | H | H |
| 8 | H | $CH_3$ | H | $NO_2$ | 23 | $OCH_3$ | H | H | H |
| 9 | $CH_3$ | H | H | H | 24 | $OCH_3$ | Cl | H | H |
| 10 | $CH_3$ | Cl | H | H | 25 | $OCH_3$ | Cl | H | $NO_2$ |
| 11 | $CH_3$ | H | Cl | H | 26 | $OCH_3$ | $CH_3$ | H | H |
| 12 | $CH_3$ | H | H | Cl | 27 | $OCH_3$ | $CH_3$ | H | Cl |
| 13 | $CH_3$ | H | H | $NO_2$ | 28 | $OCH_3$ | $CH_3$ | H | $NO_2$ |
| 14 | $CH_3$ | $CH_3$ | H | H | 29 | OH | H | H | H |
| 15 | $CH_3$ | $CH_3$ | H | Cl | 30 | OH | $CH_3$ | H | H |

TABLE 6

| Coupler No. | $R_1'$ | A |
|---|---|---|
| (IX)-1 | H | 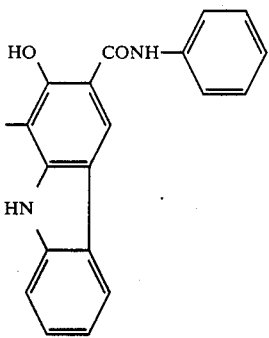 |

TABLE 6-continued
| Coupler No. | $R_1'A$ | |
|---|---|---|
| 2 | H | 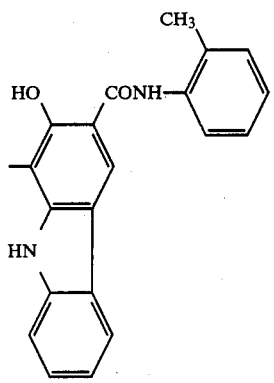 |
| 3 | $CH_3$ | 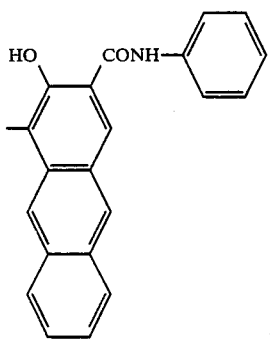 |
| 4 | H | 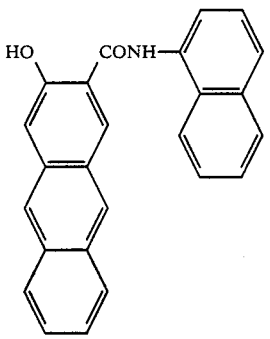 |
| 5 | H | 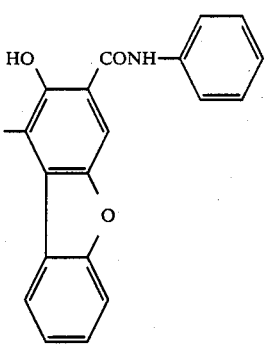 |

TABLE 6-continued
| Coupler No. | R₁'A | |
|---|---|---|
| 6 | H | 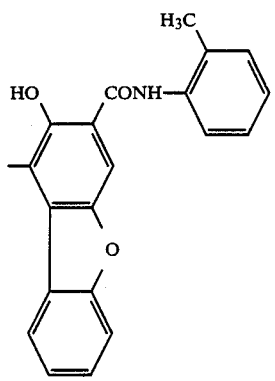 |
| 7 | H | 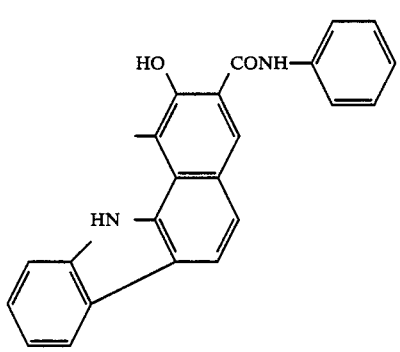 |
| 8 | H | 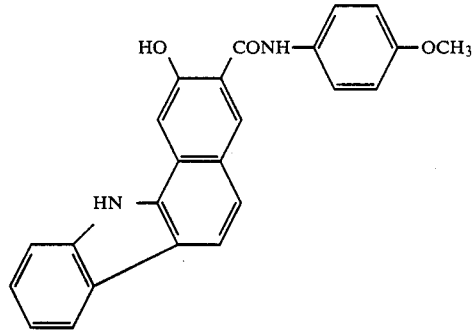 |
| 9 | H | 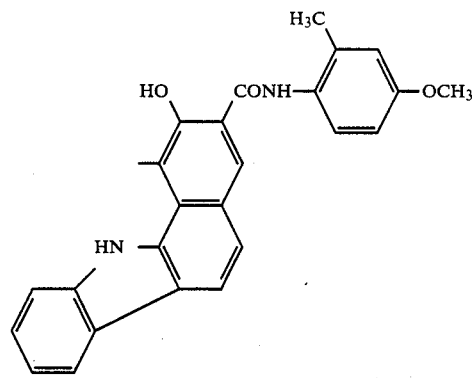 |

TABLE 6-continued

| Coupler No. | R₁'A | |
|---|---|---|
| 10 | H | (4-methyl-3-hydroxy naphthalimide, N-H) |
| 11 | H | (4-methyl-3-hydroxy naphthalimide, N-CH₃) |
| 12 | H | (4-methyl-3-hydroxy naphthalimide, N-C₂H₅) |
| 13 | H | (3-methyl-4-hydroxy naphthalimide, N-H) |
| 14 | H | (3-methyl-4-hydroxy naphthalimide, N-C₂H₅) |

What is claimed is:

1. A photoconductive coat for applying to conductive substrate comprising
  at least a styryl compound expressed by general formula [1] or [II] below and
  at least a bisazo pigment expressed by general formula [III] below:

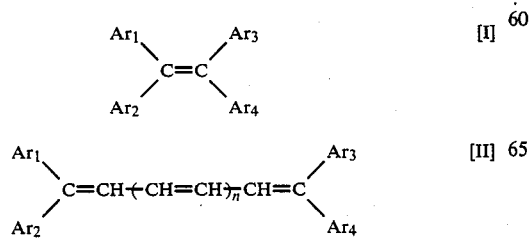

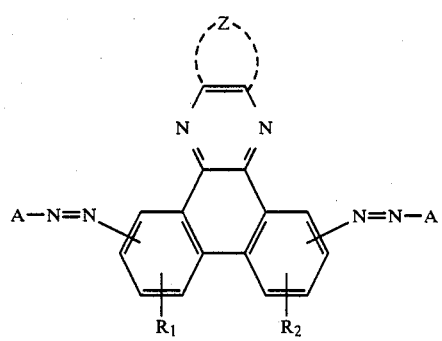

wherein each of Ar₁, Ar₂, Ar₃ and Ar₄ represents an aryl group that may possess a substituent, n is 0 or 1, each of R₁ and R₂ represents a hydrogen atom, a lower alkyl group, an allyl group, an alkoxycarbonyl group, an acyl group, a halogen atom or a monovalent organic residue, Z represents an atomic group necessary to form a substituted or non-substituted hydrocarbon or heterocyclic aromatic ring through condensation with a pyrazine ring, A represents

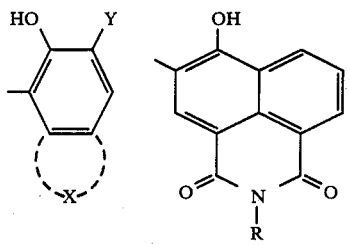

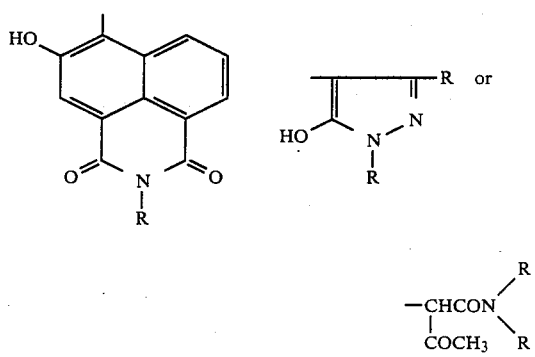

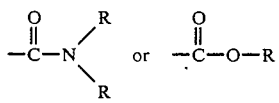

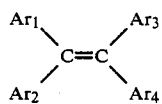

X represents an atomic group necessary to form a substituted or non-substituted hydrocarbon or heterocyclic aromatic ring through condensation with a benzene ring, Y represents $$-\overset{O}{\underset{\|}{C}}-N\overset{R}{\underset{R}{\diagdown}} \quad \text{or} \quad -\overset{O}{\underset{\|}{C}}-O-R$$

R represents a hydrogen atom, a lower alkyl group, an allyl group, an alkoxycarbonyl group, an allyloxycarbonyl group, an acyl group, a halogen atom or a monovalent organic residue that may be identical or different.

2. An electrophotosensitive article provided with a photoconductive coat comprising
at least a styryl compound expressed by general formula [I] or [II] below and
at least a bisazo pigment expressed by general formula [III] below:

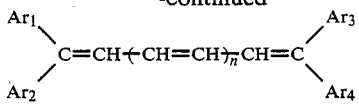 [I]

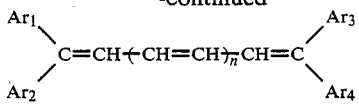 [II]

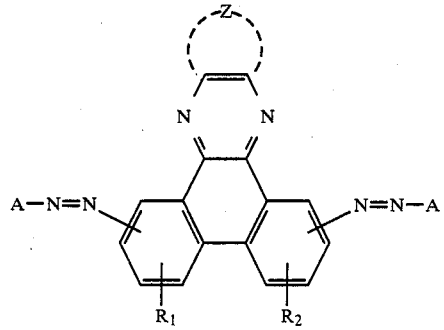 [III]

wherein each of Ar₁, Ar₂, Ar₃ and Ar₄ represents an aryl group that may possess a substituent, n is 0 or 1, each of R₁ and R₂ represents a hydrogen atom, a lower alkyl group, an allyl group, an alkoxycarbonyl group, an acyl group, a halogen atom or a monovalent organic residue, Z represents an atomic group necessary to form a substituted or non-substituted hydrocarbon or heterocyclic aromatic ring through condensation with a pyrazine ring, A represents

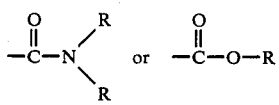

X represents an atomic group necessary to form a substituted or non-substituted hydrocarbon or heterocyclic aromatic ring through condensation with a benzene ring, Y represents $$-\overset{O}{\underset{\|}{C}}-N\overset{R}{\underset{R}{\diagdown}} \quad \text{or} \quad -\overset{O}{\underset{\|}{C}}-O-R$$

R represents a hydrogen atom, a lower alkyl group, an allyl group, an alkoxycarbonyl group, an allyloxycarbonyl group, an acyl group, a halogen atom or a monovalent organic residue that may be identical or different.

* * * * *